United States Patent
Suzuki et al.

(10) Patent No.: US 6,632,974 B1
(45) Date of Patent: Oct. 14, 2003

(54) ABSORBENT ARTICLE

(75) Inventors: Mikio Suzuki, Tochigi-ken (JP); Masao Kurahashi, Tochigi-ken (JP); Tetsuya Masuki, Tochigi-ken (JP); Akihiko Gunji, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 166 days.

(21) Appl. No.: 09/598,645

(22) Filed: Jun. 21, 2000

(30) Foreign Application Priority Data

| Oct. 7, 1999 | (JP) | .......................... 11-286693 |
| Oct. 7, 1999 | (JP) | .......................... 11-286694 |
| Dec. 22, 1999 | (JP) | .......................... 11-363897 |
| Jul. 26, 1999 | (JP) | .......................... 11-210108 |
| Jun. 21, 1999 | (JP) | .......................... 11-174592 |

(51) Int. Cl.[7] .............................................. A61F 13/15
(52) U.S. Cl. ...................................... 604/369; 604/367
(58) Field of Search ..................... 604/369, 367, 604/385.01, 358, 385.23

(56) References Cited

U.S. PATENT DOCUMENTS

| 3,911,173 A | * | 10/1975 | Sprague, Jr. ................ 427/207 |
| 3,916,900 A | | 11/1975 | Breyer et al. |
| 4,427,737 A | * | 1/1984 | Cilento et al. .............. 428/315 |
| 4,690,953 A | * | 9/1987 | Orr et al. ...................... 521/65 |
| 4,733,659 A | * | 3/1988 | Edenbaum et al. ......... 128/156 |
| 4,822,350 A | | 4/1989 | Ito et al. |
| 4,842,666 A | * | 6/1989 | Werenicz .................... 156/161 |
| 5,055,338 A | * | 10/1991 | Sheth et al. ................. 428/155 |
| 5,236,427 A | * | 8/1993 | Hamajima et al. .......... 604/378 |
| 5,331,015 A | | 7/1994 | DesMarais et al. |
| 5,405,883 A | * | 4/1995 | Park ........................... 521/98 |
| 5,462,541 A | | 10/1995 | Bruemmer et al. |
| 5,749,863 A | * | 5/1998 | Payne ......................... 604/376 |
| 6,040,494 A | * | 3/2000 | Kalentun et al. ............ 604/369 |
| 6,120,887 A | * | 9/2000 | Werenicz et al. ........... 428/219 |
| 6,198,019 B1 | * | 3/2001 | Hansson et al. ............ 604/378 |
| 6,245,697 B1 | * | 6/2001 | Conrad et al. .............. 442/370 |

FOREIGN PATENT DOCUMENTS

| EP | 0 214 292 | 3/1987 |
| EP | 0 235 949 | 9/1987 |
| EP | 0 282 771 | 9/1988 |
| EP | 0 904 755 | 3/1999 |
| GB | 2290973 | 1/1996 |
| JP | 6319769 | 11/1994 |
| WO | WO 98/00081 | 1/1998 |
| WO | WO 98/57675 | 12/1998 |
| WO | WO 00/61048 | 10/2000 |

* cited by examiner

*Primary Examiner*—Weilun Lo
*Assistant Examiner*—Jacqueline F Stephens
(74) *Attorney, Agent, or Firm*—Birch, Stewart, Kolasch & Birch, LLP (57) ABSTRACT

An absorbent article includes a liquid permeable topsheet, a liquid-impermeable and moisture-permeable leakproof sheet, and a liquid retentive absorbent member interposed between the topsheet and the leakproof sheet. A foamed material is disposed in the absorbent member. The foamed material has a density of 5 to 35 kg/m$^3$, a no-load thickness of 1 to 10 mm, and a compressive recovery of 60% or more in terms of (b/a×100), wherein a is a thickness (mm) measured after 24-hour standing with no load applied, and b is a thickness (mm) measured after 24-hour compression under a load of 180 gf/cm$^2$ followed by 30-minute standing with no load applied. The foamed material is fixed at the prescribed position with an adhesive, which has been applied to have applied parts and unapplied parts.

13 Claims, 2 Drawing Sheets

ABSORBENT ARTICLE

BACKGROUND OF THE INVENTION

1. Field of the Invention

The present invention relates to an absorbent article which is lightweight and yet has a moderate thickness to give users a feeling of assurance against leakage while worn. More particularly, it relates to an absorbent article such as a disposable diaper which is compact in a packaged state but restores its thickness on being taken out of the package for use thereby to make a user feel assured while worn and which maintains moisture permeability. The present invention also relates to an absorbent article such as a disposable diaper which hardly undergoes color change due to ultraviolet rays or nitrogen oxide gas and of which the color change, if any, is invisible from the exterior so as not to impair the appearance.

2. Description of the Related Art

The recent absorbent articles such as disposable diapers and sanitary napkins have been made more compact and easier to carry in packages by improvements added to the structure and the material. However, if absorbent articles such as disposable diapers are made thinner to make the package more compact, the absorbent article lacks stiffness and makes a user feel a fear of leakage during use. Therefore, it has been demanded to develop absorbent articles which are compact and light in their packaged state but restore their thickness when taken out of the package for use thereby giving a user a feeling of assurance while worn.

Japanese Patent Laid-Open Publication No. 51-66194 (corresponding to U.S. Pat. No. 3,916,900) discloses a disposable diaper having an elastic and wet-stable foam layer between an absorbing core and a backing sheet for confining and maintaining the absorbent core in close conformity with the perineal region of the wearer. The foam layer includes urethane foam, vinyl foam, polyvinyl chloride foam, etc. The urethane foam constituting the foam layer is interposed in its orientated state between the backing sheet and the absorbing core (cf. page 5 lower left column, lines 16–19 of the Japanese Publication). The object of the invention disclosed is to confine and maintain the absorbing core in close conformity with the perineal region of the wearer or to establish close elastic conformity of the diaper about the thighs and waist region of the wearer by taking advantage of the elasticity, compressibility, and wet stability of the urethane foam. In other words, this invention doesn't make use of the compressive recovery of urethane foam with no consideration given to a user's feeling of assurance.

Japanese Patent Laid-Open Publication No. 3-197128 discloses a three-layered superabsorbent composite structure in which the second layer is a foamed body containing superabsorbent particles. Urethane foam is used as the foamed body. The subject matter of the invention disclosed is incorporation of superabsorbent particles into a foamed body to produce a superabsorbent composite structure (an absorbent body comprising a foamed material). That is, the invention neither aims to make use of the compressive recovery of urethane foam nor to give a user an assuring feeling. Further, the foamed body having a compressive recovery function is hydrophobic. Incorporation of a particulate superabsorbent material into such a hydrophobic foamed body fails to achieve sufficient absorption performance as the structure. It is therefore necessary to separate a material performing an absorption function from a material performing a compressive recovery function.

The urethane foams described in the above cited literature are used neither to utilize their compressive recovery nor to give a user a feeling of assurance in use.

Japanese Patent Laid-Open Publication No. 6-319769 discloses an absorbent article having a baffle made of a liquid impermeable foamed material having a thickness of 0.51 to 1.54 mm and a density of 0.0225 to 0.0962 g/cm$^3$. In this absorbent article, the baffle is not used as a compression recovering sheet but as a liquid impermeable backsheet. Therefore, the article is not to present both compactness when packaged and a feeling of assurance in use. Further, the foamed material is, being cellular (porous), sometimes likely to leak so that it is cannot be said to have necessary functions as a backsheet.

On the other hand, such materials as ink, adhesives, plastics and rubber, generally used in absorbent articles such as disposable diapers and sanitary napkins tend to undergo color change by ultraviolet rays on long-term exposure to sunlight to deteriorate the appearance.

For example, it is known that the urethane foams described in the above literature are yellowed or browned by ultraviolet rays. Where a urethane foam is disposed between a leakproof sheet and an absorbent member, between a topsheet and an absorbent member, inside an absorbent member or in their plural positions of a disposable diaper, etc., only the urethane foam undergoes yellowing to impair the outer appearance when the article is exposed to sunlight for a long period of time or when the article is placed near a fan heater in winter and exposed to nitrogen oxide gas emitted from the fan heater. The yellowed urethane foam is easily perceived particularly in a lightweight disposable diaper of which the members adjacent to the urethane foam, such as the topsheet or the leakproof sheet are made thin. Even where the urethane foam is inside the absorbent member, since a lightweight diaper contains a reduced amount of pulp, the color change will be detected through the adjacent member. Improvement in this respect has therefore been desired. In particular, since the urethane foam described in the 66194/76 supra is a relatively large member in a sanitary napkin, the color change will considerably ruin the appearance of the napkin, giving a user discomfort.

In an attempt to prevent urethane foam from yellowing, it has been suggested to add various stabilizers such as ultraviolet absorbers, antioxidants and piperidine compounds, or to add or apply white pigments such as titanium white. However, these conventional methods are still unsatisfactory in preventing yellowing of urethane foam.

Not only ultraviolet rays but chemical substances, such as nitrogen oxide ($NO_x$) gas, are contributory to the color change. Therefore, the problem of color change cannot be resolved by methods paying attention only to color change by ultraviolet rays.

SUMMARY OF THE INVENTION

An object of the present invention is to provide an absorbent article which is thin and compact in a packaged state but restores its thickness on being taken out of the package for use thereby to make a user feel assured while worn.

Another object of the present invention is to provide an absorbent article containing a material susceptible to color change, such as urethane foam, in which the material hardly undergoes color change by ultraviolet rays or $NO_x$ gas, or the color change, if any, of the material is invisible from the exterior so as not to impair the appearance.

The above objects are accomplished by an absorbent article comprising a liquid permeable topsheet, a liquid-impermeable and moisture-permeable leakproof sheet, and a liquid retentive absorbent member interposed between the topsheet and the leakproof sheet, wherein a foamed material is disposed between the leakproof sheet and the absorbent member, between the topsheet and the absorbent member, inside the absorbent member or in plural positions thereof, the foamed material having a density of 5 to 35 kg/m$^3$, a no-load thickness of 1 to 10 mm, and a compressive recovery of 60% or more in terms of (b/a×100), wherein a is a thickness (mm) measured after 24-hour standing with no load applied, and b is a thickness (mm) measured after 24-hour compression under a load of 180 gf/cm$^2$ followed by 30-minute standing with no load applied, and the foamed material is fixed at the prescribed position with an adhesive which has been applied to substantially the entire surface of at least one side of the foamed material or substantially the entire contact area of a member to be brought into contact with the foamed material in such a manner that the adhesive is distributed substantially uniformly while providing applied parts and unapplied parts.

The compressive recovery can be measured as follows.
Method of Compressive Recovery Measurement:

The thickness of a foamed material after being allowed to stand for 24 hours under no load (the thickness before compression) is taken as a (mm). The thickness of the foamed material after being compressed under a load of 180 gf/cm$^2$ (17.6 kPa) for 24 hours and then, after the load is removed, allowed to stand for 30 minutes is taken as b (mm). Compression recovery is defined to be b/a×100 (%). Thickness measurement is made with a laser displacement sensor PA-1830, supplied by Keyence Corp., and an average is obtained in a usual manner.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be more particularly described with reference to the accompanying drawings, in which.

DETAILED DESCRIPTION OF THE PREFERRED EMBODIMENTS

A disposable diaper 1 according to a preferred embodiment of the present invention is shown in FIGS. 1 through 4. The disposable diaper 1 has a liquid permeable topsheet 2, a liquid impermeable and moisture permeable leakproof sheet 3, and a liquid retentive absorbent member 4 interposed between the sheets 2 and 3. A pair of fastening tapes 11 are provided on both sides B1 and B2 of the rear waist portion B.

In detail, as shown in FIGS. 1 to 4, the disposable diaper 1 according to this embodiment comprises an absorbent member 4, a leakproof sheet 3 which is approximately of the same size as the absorbent member 4, and a topsheet 2 which is disposed to cover the upper surface and both sides of the absorbent member 4. An outer nonwoven fabric layer 5 is disposed on the outer side of the leakproof sheet 3. A water-repellent nonwoven fabric strip 61 is provided on the topsheet 2 on both sides of the absorbent member 4 to form upstanding gathers 6. Both the outer nonwoven fabric layer 5 and the water-repellent nonwoven fabric strip 61 extend laterally from each side of the absorbent member 4, and leg elastic members 71 are held therebetween at the extension to form a pair of leg gathers 7. The free end 62 of each water-repellent nonwoven fabric strip 61 has an elastic member 63 to form upstanding gathers 6. The outer nonwoven fabric layer 5 and the topsheet 2 both extend from the longitudinal ends of the disposable diaper 1 to form a pair of waist portions 8. The waist portions 8 each has an waist elastic member 81 of band form sandwiched between the extended topsheet 2 and the extended outer nonwoven fabric layer 5. The absorbent member 4 is composed of bulky nonwoven fabric 41 holding an absorbent polymer 42 in the interstices among the constituent fibers and supporting paper 43 wrapping the bulky nonwoven fabric 41. The outer nonwoven fabric layer 5 has on the front waist portion A thereof a landing tape 51 on which the fastening tapes 11 are to be fixed.

The disposable diaper of the present embodiment has a foamed material having a specific density, a specific no-load thickness, and a specific compressive recovery in a prescribed position.

Figure 1:
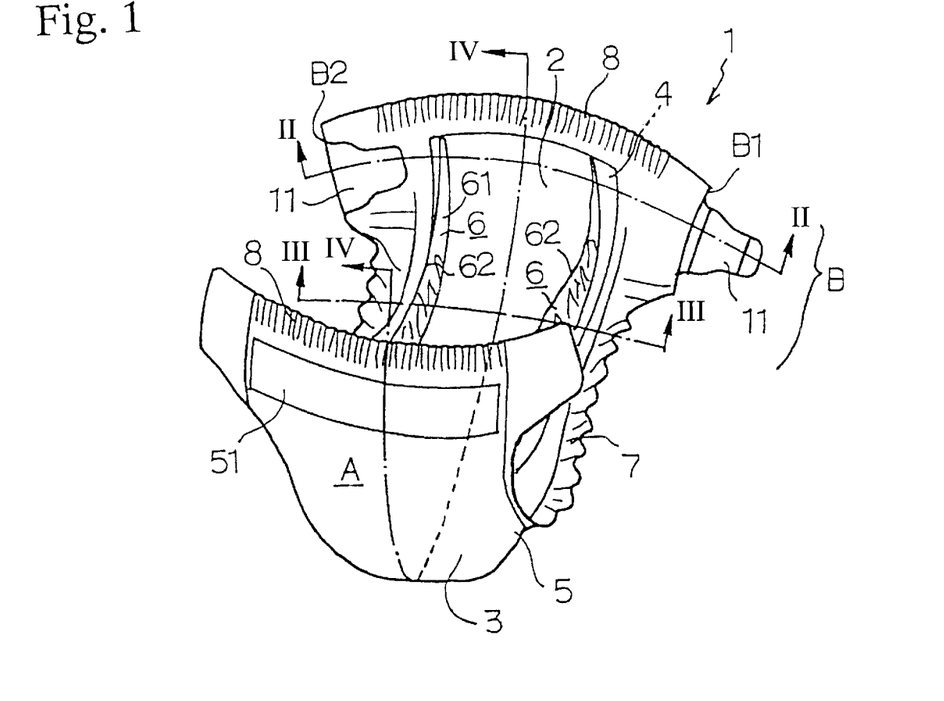
FIG. 1 is a perspective view depicting an embodiment of a disposable diaper as an absorbent article of the present invention.
Figure 2:
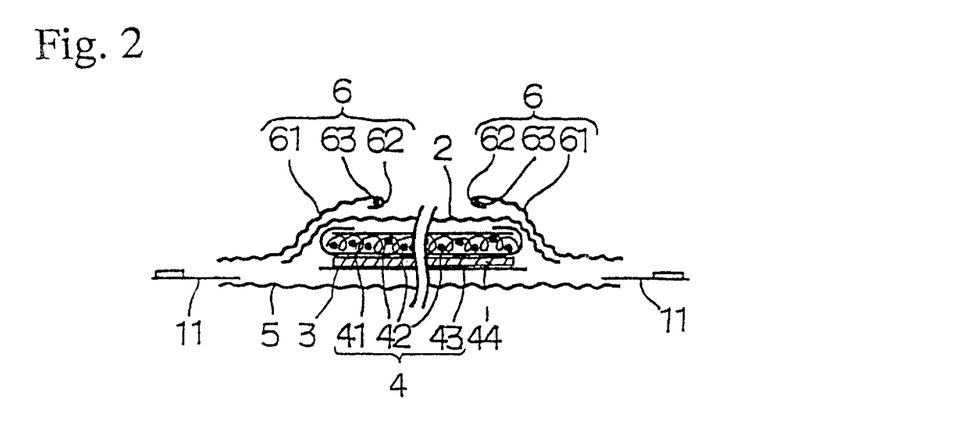
FIG. 2 is a schematic cross sectional view, taken along II—II line of FIG. 1.
Figure 3:
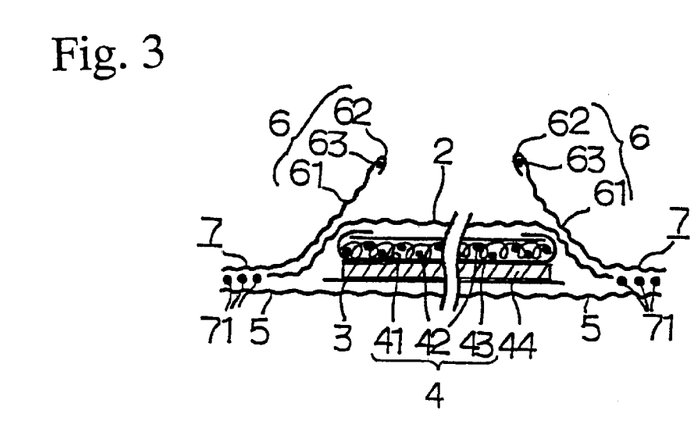
FIG. 3 is a schematic cross sectional view, taken along III—III line of FIG. 1.
Figure 4:
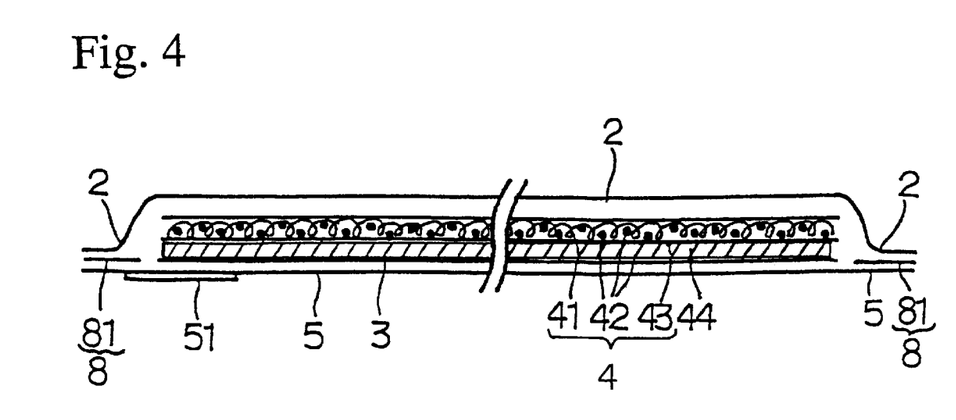
FIG. 4 is a schematic cross sectional view, taken along IV—IV line of FIG. 1.

The foamed material can be disposed between the leakproof sheet and the absorbent member, between the topsheet and the absorbent member or inside the absorbent member. The foamed material may be disposed in two or more of these positions. Having the foamed material in this way, the disposable diaper is light and thin in a package and restores its thickness when taken out of the package. In this particular embodiment shown, the foamed material 44 is arranged between the leakproof sheet 3 and the absorbent member 4 as shown in FIGS. 2 to 4.

The foamed material is fixed in the prescribed position with an adhesive. The adhesive is applied to substantially the entire surface of at least one side of the foamed material or substantially the entire contact surface of a member to be brought into contact with the foamed material (i.e., the leakproof sheet, the supporting paper containing the absorbent member, the topsheet, and the like, hereinafter referred to as a contact member) substantially uniformly in such a manner as to provide coated parts and uncoated parts. Thus, the at least one side of the foamed material is fixed onto substantially the entire surface of the contact area (adherend surface) of the contact member while retaining breathability of the disposable diaper. The recovery function possessed by the foamed body directly acts on the disposable diaper, that is, the fixed foamed body is compressed to make the disposable diaper compact in a package and allowed to expand on use to give a user a feeling of assurance. If at least one side of the foamed material is not fixed to substantially the entire adherend surface of the contact member, the compressive recovery action is hardly executed, and wrinkles occur in a package (under compression) mainly in the contact member side in the positions corresponding to the non-adhered parts, which impairs not only the appearance but the performance of the diaper in use.

The adhesive 5 which can be used include rubber adhesives, such as solvent type rubber adhesives, emulsion type rubber adhesives, hot-melt type rubber adhesives; olefin adhesives such as hot-melt type olefin adhesives; and acrylic adhesives, such as solvent type acrylic adhesives and emulsion type acrylic adhesives.

The rubber adhesives are prepared by blending an elastomer as a base polymer with a tackifier and a softener. The elastomer includes styrene-butadiene rubber (SBR), a styrene-butadiene-styrene block copolymer (SBS), a styrene-isoprene-styrene block copolymer (SIS), a styrene-ethylene-butylene-styrene block copolymer (SEBS), a styrene-ethylene-propylene-styrene block copolymer (SEPS), natural rubber, and synthetic isoprene rubber. The tackifier includes $C_5$ cut petroleum resins, $C_9$ cut petroleum resins, dicyclopentadiene petroleum resins, rosin petroleum resins, polyterpene resins, terpene phenol resins, and hydrogenation products of these resins. Useful commercially available tackifiers include hydrogenated terpene resins such as Clearon available from Yasuhara Kagaku K.K., and hydrogenated aromatic petroleum resins such as Alcon available from Arakawa Kagaku K.K. The softeners include process oils, mineral oils, various plasticizers, polybutene, and liquid tackifying resins each having a softening point of 10° C. or lower and an average molecular weight of 200 to 700. Specific examples of useful softeners include paraffinic oils, such as Shell Flex available from Shell Chemical Company and PW-90 available from Idemitsu Kosan, and ester oils, such as tetraoctyl pyromellitate, didodecyl phthalate, and trioctyl trimellitate.

The solvent type rubber adhesives are prepared by dissolving the above-mentioned components (i.e., the elastomer, the tackifier, and the softener) in an organic solvent such as toluene, ethyl acetate and heptane. The elastomer is preferably used in an amount of 10 to 100 parts by weight, particularly 20 to 70 parts by weight, per 100 parts by weight of the total amount of the tackifier and the softener. The tackifier and the softener are preferably used in an amount of 50 to 90 parts by weight (particularly 60 to 90 parts by weight) and 10 to 50 parts by weight (particularly 10 to 40 parts by weight), respectively, totally amounting to 10 to 100 parts by weight. In order for the solvent type rubber adhesive to exhibit sufficient adhesive strength for fixing the foamed material, it preferably comprises 10 to 40% by weight (particularly 10 to 30% by weight) of the elastomer, 30 to 70% by weight (particularly 40 to 70% by weight) of the tackifier, and 10 to 50% by weight (particularly 10 to 40% by weight) of the softener.

The emulsion type rubber adhesives are prepared by dispersing the above-described components in water. The elastomer is preferably used in an amount of 10 to 100 parts by weight, particularly 20 to 70 parts by weight, per 100 parts by weight of the total amount of the tackifier and the softener. The tackifier and the softener are preferably used in an amount of 50 to 90 parts by weight (particularly 60 to 90 parts by weight) and 10 to 50 parts by weight (particularly 10 to 40 parts by weight), respectively, totally amounting to 100 parts by weight. In order for the emulsion type rubber adhesive to exhibit sufficient adhesive strength for fixing the foamed material, it preferably comprises 10 to 40% by weight (particularly 10 to 30% by weight) of the elastomer, 30 to 70% by weight (particularly 40 to 70% by weight) of the tackifier, and 10 to 40% by weight (particularly 10 to 30% by weight) of the softener.

The hot-melt type rubber adhesives are prepared by melt blending the above-mentioned components. The elastomer is preferably used in an amount of 10 to 100 parts by weight, particularly 20 to 70 parts by weight, per 100 parts by weight of the total amount of the tackifier and the softener. The tackifier and the softener are preferably used in an amount of 50 to 90 parts by weight (particularly 60 to 90 parts by weight) and 10 to 50 parts by weight (particularly 10 to 40 parts by weight), respectively, totally amounting to 100 parts by weight. In order for the hot-melt type rubber adhesive to exhibit sufficient adhesive strength for fixing the foamed material, it preferably comprises 10 to 40% by weight (particularly 10 to 30% by weight) of the elastomer, 30 to 70% by weight (particularly 40 to 70% by weight) of the tackifier, and 10 to 40% by weight (particularly 10 to 30% by weight) of the softener. It is preferred to use an antioxidant in addition to the elastomer, the tackifier, and the softener in order to prevent deterioration of these components by the heat of melt blending. Suitable antioxidants include phenol antioxidants, amine antioxidants, phosphorus antioxidants, and benzimidazole antioxidants. The antioxidant is preferably added in an amount of 0.1 to 3 parts, particularly 0.3 to 2 parts, by weight per 100 parts by weight of the total amount of the elastomer, the tackifier, and the softener.

The hot-melt type olefin adhesives can comprise solely of an amorphous poly-α-olefin (hereinafter APAO). APAO includes a propylene-ethylene copolymer, a propylene-butene-1 copolymer, and a propylene-hexene copolymer, which are commercially available under trade names Ubetac (supplied by Ube Rexene Co., Ltd.) and East Flex (available from Eastman Kodak Co.). APAO also includes a propylene-ethylene-butene-1 terpolymer, which is commercially available under a trade name Best Plast (supplied from Hultz).

The hot-melt type olefin adhesives also include those prepared by melt blending APAO with the same tackifier and the same softener as used in the above-described rubber adhesives and the same antioxidant as used in the above-described hot-melt type rubber adhesives. To secure sufficient adhesive strength for fixing the foamed material and to prevent thermal deterioration of APAO, the tackifier and the softener, it is preferred that APAO be used in an amount of 20 to 60% by weight (particularly 30 to 60% by weight); the tackifier 30 to 70% by weight (particularly 30 to 60% by weight); the softener 0 to 30% by eight (particularly 5 to 30% by weight); and the antioxidant 0.1 to 3% by weight (particularly 0.3 to 2% by weight).

The acrylic adhesives are prepared by copolymerizing a monomer, a comonomer, and a functional group-containing monomer. The monomer includes ethyl acrylate, butyl acrylate, and 2-ethylhexl acrylate. The comonomer includes vinyl acetate, acrylonitrile, acrylamide, methyl methacrylate, and methyl acrylate. The functional group-containing monomer includes maleic anhydride, acrylic acid, and methacrylic acid.

The solvent type acrylic adhesives are prepared by homogeneous polymerization of the monomer mixture (a monomer, a comonomer, and a functional group-containing monomer) in an organic solvent, such as toluene, ethyl acetate, and heptane, in a conventional manner. The emulsion type acrylic adhesives are prepared by emulsion polymerization of the monomer mixture in water in a conventional manner.

Of the solvent type, emulsion type or hot-melt type rubber adhesives, the hot-melt type olefin adhesives and the solvent type or emulsion type acrylic adhesives, preferred are hot-melt type adhesives, i.e., hot-melt type rubber adhesives and hot-melt type olefin adhesives. The hot-melt type rubber adhesives, which exhibit high adhesive strength, are particularly preferred. By use of the hot-melt adhesives in fixing the foamed material to a prescribed position, improved productivity of the absorbent article is obtained, and there arises no problem of solvent remaining. In the present embodiment, a hot-melt type rubber adhesive is used for adhering the foamed material 44.

It is preferred for the hot-melt adhesive used to have a melt viscosity of 10,000 mPa·s or less, particularly 1,000 to 8,000 mPa·s, especially 1,000 to 6,000 mPa·s, at 180° C. Where the hot-melt adhesive is applied in an atomized state in a non-contact system, uneven coating or dripping can be prevented as long as it has a melt viscosity of 10,000 mPa·s or less.

The hot-melt adhesive is preferably applied in an amount of 1 to 30 g/m$^2$, particularly 3 to 10 g/m$^2$, to secure improved adhesion of the foamed material and to prevent blocking due to oozing of the applied adhesive or dripping. In using other types of adhesives than the hot-melt type, it is similarly preferred to secure improved adhesion of the foamed material that the dry coating weight (weight after evaporation of the organic solvent or water) be 1 to 30 g/m$^2$, particularly 3 to 10 g/m$^2$.

The hot-melt adhesive can be applied either in a contact system in which a hot-melt coater head is in contact with an adherend (i.e., the foamed material or the contact member), exemplified by slot coating or porous coating; or in a non-contact system in which the adhesive is atomized, exemplified by slot spraying, curtain spraying, melt-blowing or spiral spraying. The non-contact system is preferred because of less damage to the adherend and uniformity in making coated parts. Other types of adhesives can be applied either in a non-contact system (e.g., slot spraying) or a contact system using a patterned roll (e.g., gravure roll coating or reverse roll coating).

The configuration of the coated parts with the adhesive includes, but is not limited to, spots, lines, dots, and spirals, which are preferred for uniformly fixing the foamed material while securing breathability. A preferred area ratio of the coated parts to the uncoated parts is 2/8 to 7/3, particularly 3/7 to 6/4.

The coated parts are uniformly distributed over the contact area of the foamed material or the contact member. Where the coated parts are spots, each spot preferably has a diameter of 0.3 to 2 mm, particularly 0.5 to 1 mm, and the density of the spots is preferably 9 to 400, particularly 25 to 100, per cm$^2$. Where the coated parts are lines, each line preferably has a thickness of 0.01 to 0.5 mm, particularly 0.05 to 0.1 mm. The density of the lines is preferably 10 to 40, particularly 10 to 30, per centimeter of a straight line drawn at right angles with an arbitrarily chosen line of the applied adhesive. Where the coated parts are dots, the dot density is preferably 9 to 400, particularly 25 to 100, per cm$^2$. Where the coated parts are spirals, the thickness of the spiral is preferably 0.05 to 1 mm, particularly 0.1 to 0.5 mm.

The foamed material which can be used in the present invention has a density of 5 to 35 kg/m$^3$, particularly 5 to 20 kg/m$^3$. A foamed material having a smaller density than 5 kg/m$^3$ is difficult to make. A foamed material having a density greater than 35 kg/m$^3$ is too hard to make the package of the absorbent article compact and also ineffective to reduce the weight of the absorbent article. The density of the foamed material is obtained from the thickness, length and weight measured after the sample is allowed to stand for 24 hours with no load applied.

The foamed material used in the present invention has a no-load thickness of 1 to 10 mm, preferably 1.7 to 5 mm. A foamed material thinner than 1 mm is too flimsy to produce the compressive recovery effect. A foamed material thicker than 10 mm is too bulky and inconvenient to use when allowed to expand. The no-load thickness is measured with a laser displacement sensor PA-1830, supplied by Keyence Corp., in a usual manner. The foamed material with the above-specified thickness can preferably be compressed to a thickness of 0.2 to 3 mm, still preferably 0.3 to 1 mm.

The foamed material used in the present invention has a compressive recovery of 60% or greater, preferably 70% or greater, particularly preferably 90% or greater. If the compressive recovery is less than 60%, the package of the absorbent article can be made compact, but the article does not recover the thickness sufficiently to make the user feel assured. The compressive recovery can be measured by the aforementioned method.

The foamed materials include those formed by making use of gas generated on chemical reaction or by injecting a low-boiling solvent, such as Freon, or air. Urethane foam (polyurethane foam) and polyolefin foam can be used. Urethane foam is preferred for obtaining a high compressive recovery. Ether type urethane foam is still preferred for obtaining a low density foam, with which lightweight disposable diapers showing good recovery from compression can be obtained. However, as stated previously, urethane foam is disadvantageous in that it easily undergoes color change by ultraviolet rays or NO$_x$ gas (inclusive of NO, NO$_2$, etc.).

In order to prevent color change, it is preferred for the urethane foam to have an yellowness index (hereinafter referred to as a YI) of 40 or smaller, particularly 35 or smaller, especially 30 or smaller, when left to stand in 200 ppm nitrogen monoxide for 5 hours and when irradiated with ultraviolet rays in a carbon arc fadeometer for 24 hours. Urethane foam having an YI of 40 or smaller hardly undergoes yellowing when exposed to NO$_x$ in the environment, e.g., when placed near a fan heater, or to ultraviolet rays in the environment, e.g., under sunlight, for a long time. Or, the degree of yellowing, if any, is such as is imperceptible from the exterior with the urethane foam being used in a disposable diaper. If the YI exceeds 40, the yellowing is visible from the outside to such a degree as impairs the appearance of the diaper. The YI can be measured in accordance with JIS K 7103:1977.

In a highly preferred embodiment, the urethane foam contains as stabilizers (1) an ultraviolet absorber, (2) a tertiary phosphorous ester represented by formula (I) shown below and having a phosphorus content of 4 to 14% by weight, and (3) a 1,1-dialkyl-substituted semicarbazide or carbazinic acid ester having a moiety represented by formula (II), (III) or (IV) shown below. The urethane foam containing such stabilizers is markedly prevented from yellowing and easily secure a YI smaller than 40. Such effects are attributed to the synergism of the combination of the stabilizers (1), (2) and (3).

(I)

wherein R$_1$, R$_2$, and R$_3$, which may be the same or different, each represent an alkyl group, a cycloalkyl group, an aryl group, an alkylaryl group or an arylalkyl group.

wherein $R_4$ and $R_5$, which may be the same or different, each represent a substituted or unsubstituted alkyl group having 1 to 10 carbon atoms, or $R_4$ and $R_5$ are taken together to form a ring which may contain a hetero atom.

Examples of the ultraviolet absorbers (1) are described in Japanese Patent Publication No. 5-79105, column 4, lines 8–24. Preferred of them are 2-(2'-hydroxy-5'-methylphenyl)benzotriazole, 2-(2'-hydroxy-3',5'-di-t-butylphenyl)benzotriazole, and a 2-(2'-hydroxy-3',5'-dialkylphenyl)benzotriazole. These ultraviolet absorbers (1) are used either individually or as a mixture of two or more thereof in combination with the tertiary phosphorous ester (2) and the 1,1-dialkyl-substituted semicarbazide or carbazinic acid ester (3).

The tertiary phosphorous ester (2) is represented by formula (1) and has a phosphorus content of 4 to 14% by weight. Tertiary phosphorous esters having a phosphorus content of 6 to 8% by weight are particularly preferred, such as triisodecyl phosphite, phenylisodecyl phosphite, diphenylnonylphenyl phosphite, and triisooctyl phosphite. These tertiary phosphorous esters are used either individually or as a mixture of two or more thereof in combination with the ultraviolet absorber (1) and the 1,1-dialkyl-substituted semicarbazide or carbazinic acid ester (3). The phosphorus content of the tertiary phosphorous ester is obtained by the method described in Japanese Patent Publication No. 5-79105, column 7 line 27 to column 8 line 13.

The 1,1-dialkyl-substituted semicarbazide or carbazinic acid ester (3) contains the moiety of formula (II), (III) or (IV). Examples of such compounds are described in Japanese Patent Publication No. 5-79105, column 5 line 24 to column 7 line 22. Particularly preferred of them are 1,6-hexamethylenebis(N,N-dimethylsemicarbazide) (referred to as compound A in the 79105/93), 1,1,5,5-tetramethylcarbohydrazide (compound G), phenyl N-morpholinocarbazinate (compound Y), phenyl 1,1-dimethylcarbazinate (compound Z), 1,6-hexamethylenebis(N-morpholinocarbazide) (compound J), and 1,6-hexamethylenebis(N,N-cyclopentylenesemicarbazide) (compound I). These 1,1-dialkyl-substituted semicarbazides or carbazinic acid esters (3) are used either individually or as a mixture of two or more thereof in combination with the ultraviolet absorber (1) and the tertiary phosphorous ester (2).

The ultraviolet absorber (1), the tertiary phosphorous ester (2), and the 1,1-dialkyl-substituted semicarbazide or carbazinic acid ester (3) are each preferably added in an amount of 0.05 to 5% by weight, particularly 0.1 to 3% by weight, based on the polyurethane forming the urethane foam from the viewpoint of the effect of stability and improvement of physical properties such as product strength and stretchability.

The above-described stabilizers (1), (2) and (3) can be incorporated into the urethane foam by previously dispersing in part of the raw materials of the urethane foam or adding to the heated raw materials of the urethane foam.

The urethane foam is prepared from a polyisocyanate and an active hydrogen-containing compound. The polyisocyanate includes polyisocyanate compounds such as tolylene diisocyanate and 4,4'-diphenylmethane diisocyanate, or mixtures thereof, modification products thereof, or prepolymers thereof. The active hydrogen-containing compounds include polyol compounds, preferably polyester polyols and/or polyether polyols having two or more hydroxyl groups per molecule.

The urethane foam is produced by, for example, mixing a polyol component to which the ultraviolet absorber and the 1,1-dialkyl-substituted semicarbazide or carbazinic acid ester have been added and an isocyanate component to which the tertiary phosphorous ester has been added, stirring the mixture, and letting the mixture foam spontaneously.

If desired, the urethane foam can contain various additives, such as chain extenders, catalysts, blowing agents, colorants, inorganic fillers, foam stabilizers, antioxidants, and light stabilizers.

The leakproof sheet used in the present embodiment is made of a moisture permeable sheet material (the term "sheet material" as used hereunder denotes the moisture permeable sheet material). Breathability of the disposable diaper can be secured by using the moisture permeable sheet material as a leakproof sheet and by applying the adhesive for fixing the foamed material in the above-described specific manner that the adhesive is distributed substantially uniformly while providing coated parts and uncoated parts. It is preferred for the sheet material to have a moisture permeability of 0.5 to 4 g/(100 cm$^2$·hr), particularly 1.0 to 2.5 g/(100 cm$^2$·hr). With this preferred moisture permeability, creation of a humid environment in the inner side of the disposable diaper while worn and resultant skin irritation are prevented sufficiently while preventing leakage of urine, etc. The moisture permeability as referred to herein is the value measured in accordance with JIS Z0208.

It is preferred for the sheet material to have an ultraviolet transmittance of 10% or less. When used to cover the part of the disposable diaper that is liable to color change, the sheet material having an ultraviolet transmittance of 10% or less suppresses transmittance of ultraviolet rays thereby to suppress ultraviolet-induced color change of the covered part. The sheet material is particularly effective in suppressing yellowing of urethane foam used as the foamed material. A preferred ultraviolet transmittance is 8% or less, particularly 5% or less. The ultraviolet transmittance is preferably as close to zero as possible with no lower limit. The ultraviolet transmittance is measured at a wavelength of 380 nm with a UV spectrophotometer MPS-2000, manufactured by Shimadzu Corp.

It is preferred for the sheet material to have a whiteness of 65 or more, particularly 68 or more, especially 70 or more, and a total light transmittance of 35% or less, particularly 33% or less, especially 30% or less. The sheet material having these preferred attributes exhibits enhanced masking power so that any color change of the covered part, which may have developed by the action of chemical substances such as NO$_x$ gas, can be made invisible from the outside and thereby prevented from giving the cause for deterioration of the diaper appearance. This is specially effective in using urethane foam as the foamed material.

The whiteness is measured in accordance with JIS Z 8722 by means of, e.g., a color difference meter SZ-Σ80 (a W(Lab) value is taken as a whiteness) supplied by Nippon Densyoku Kogyo K.K. The total light transmittance is measured over a visible wavelength region of 380 to 800 nm according to JIS K 7105 with, e.g., a haze-transmittance-reflectance meter HR-100 supplied by Murakami Shikisai Gijutsu Kenkyusho.

It is preferred for the sheet material to have not only the above-specified moisture permeability but a water pressure resistance of 4.9 kPa or higher, particularly 10 kPa or higher, especially 10 to 20 kPa or higher, for prevention of humid environment creation and skin irritation. The upper limit of the water pressure resistance is decided with the balance with moisture permeability being taken into consideration. The maximum water pressure resistance practically achieved is about 30 kPa. The water pressure resistance can be measured according to Method A of Hydrostatic Pressure Test specified in JIS L 1092.

The sheet material preferably has a thickness of 10 to 100 $\mu$m, particularly 15 to 50 $\mu$m, from the standpoint of the diaper's being compact and convenient to use.

The sheet material preferably comprises thermoplastic resin, particularly a polyolefin resin, as a main component. Examples of useful polyolefin resins are described, e.g., on page 3 column 3 lines 1–29 of Japanese Patent Laid-Open Publication No. 9-268234, which is in relation to the prior application filed by the Assignee, and they can be used either individually or as a combination of two or more thereof. From the standpoint of softness, strength and stretchability, linear low-density polyethylene is used for preference. The sheet material preferably contains the polyolefin resin in a proportion of 10 to 50%, particularly 20 to 45%, by weight from the viewpoint of strength and moisture permeability.

In order that the sheet material may fulfill the above-specified preferred conditions of ultraviolet transmittance, total light transmittance, and whiteness, it is preferred the sheet material contains titanium oxide. A preferred titanium oxide content is 1 to 25% by weight, particularly 2 to 20% by weight, for satisfying the above requirements and also for securing sufficient sheet strength. It is preferred for obtaining high hiding powder and making the sheet material thickness uniform that titanium oxide to be used has a particle size of 0.1 to 1.0 $\mu$m, particularly 0.2 to 0.4 $\mu$m.

For reducing the ultraviolet transmittance, the sheet material preferably contains 0.2 to 1.0% by weight, particularly 0.3 to 0.6% by weight, of ultraviolet absorbers. Addition of less than 0.2% by weight of an ultraviolet absorber hardly produces substantial effect, and more than 1.0% by weight tends to deteriorate sheet molding properties. Ultraviolet absorbers which are preferred for ultraviolet absorbing performance and molding properties include salicylic acid compounds, such as phenyl salicylate, benzophenone compounds, such as 2,4-dihydroxybenzophenone, benzotriazole compounds, such as 2-(2'-hydroxy-3'-t-butyl-5'-methylphenyl)-5-chlorobenzotriazole, and cyanoacrylate compounds, such as 2-ethylhexy 2-cyano-3,3'-diphenylacrylate.

In order for the sheet material to have the above-specified preferred moisture permeability, the sheet material preferably contains inorganic fillers except titanium oxide. Useful inorganic fillers are described, e.g., in Japanese Patent Laid-Open Publication No. 9-268234, page 3 column 4 lines 9–42. These compounds can be used either individually or as a mixture of two or more thereof. For obtaining high moisture permeability and sufficient sheet strength, a preferred inorganic filler content is 10 to 80% by weight, particularly 20 to 70% by weight. The inorganic filler to be added preferably has an average particle size of 50 $\mu$m or smaller, particularly 10 $\mu$m or smaller, especially from 0.5 to 5 $\mu$m. Particles greater than 50 $\mu$m in average diameter reduce the pore denseness, and liquid tends to ooze from the resulting sheet. Particles smaller than 0.5 $\mu$m in average diameter have poor dispersibility in the resin composition, and the resin composition tends to have poor molding properties.

The sheet material preferably contains a plasticizer (or softener) to have improved dispersibility for the inorganic filler. Examples of useful plasticizers are described on page 3 column 3 line 36 to column 4 line 2 of Japanese Patent Laid-Open Publication No. 5-230252, which is in relation to the prior application filed by the Assignee. Plasticizers which has not only the function of plasticizing resins but the function of uniformly dispersing inorganic fillers are particularly preferred; for dispersing effects would be obtained without separately adding a dispersant. Plasticizers preferred from this point of view are fatty acid alcohol esters, fatty acid amides, ketone resins, silicone oils, and so forth. The plasticizer is preferably added in an amount of 0.1 to 20% by weight, particularly 1 to 10% by weight, based on the weight of the sheet material. If the amount of the plasticizer is less than 0.1% by weight, the effect of addition tends to be insubstantial. If added in amounts exceeding 20% by weight, the plasticizer tends to bleed out to deteriorate the texture or to cause adhesion failure.

In addition to the above-described components (polyolefin resin, titanium oxide, ultraviolet absorber, inorganic filler and plasticizer), the sheet material can contain other additives, such as antioxidants, stabilizers and colorants, if desired. The amount of these additives to be added is preferably 0.01 to 10% by weight, particularly 0.1 to 5% by weight, based on the weight of the sheet material.

From the aspect of physical properties and cost, the sheet material is preferably prepared by molding a film from a resin composition comprising the above-described components (polyolefin resin, titanium oxide, ultraviolet absorber, inorganic filler, plasticizer, etc.) and orientating the resulting film. In detail, the resin composition is kneaded and pelletized by means of a twin-screw extruder, etc., extrusion-molding the pellets into a film through a circular die, and orientating the film in at least one direction by means of a tenter, etc. to form a great number of fine pores, as described, for example, in Japanese Patent Laid-Open Publication No. 9-268234, page 4 column 6 line 30 to page 5 column 7 line 12. The resulting sheet thus prepared can have its moisture permeability and water pressure resistance controlled within the above-described respective preferred ranges and can have a reduced total light transmittance.

Since the leakproof sheet 3 of the disposable diaper 1 according to the present embodiment is made of the aforementioned sheet material having a low ultraviolet transmittance, a high whiteness, a low total light transmittance, a moderate moisture permeability and a high water pressure resistance, it has now been made possible without requiring a complicated structure that the foamed material 44 can be inhibited from color change by ultraviolet rays, that the color change of the foamed material 44, if any, by $NO_x$, etc. is hardly perceived from the exterior and thereby prevented from impairing the appearance of the diaper, and that creation of a humid internal environment and resultant skin irritation are effectively prevented in the practical use.

Materials forming the other members constituting the disposable diaper having the above-described structure are briefly explained. The topsheet, the absorbent member, the water-repellent nonwoven fabric, and the outer nonwoven fabric can be of any materials generally employed in disposable diapers. The elastic members used in the leg portions, the upstanding gathers, and the waist portions can also be of any materials generally used in disposable diapers. The fastening tapes include a tape coasted with an adhesive and a male member of a mechanical fastener. The landing tape on which the fastening tapes are to be fixed includes a release tape (used in combination with an adhesive tape) and a female member of the mechanical fastener (used in combination with the male member).

In order to give a user an enhanced feeling of assurance, it is preferable that the thickness of the disposable diaper according to the present embodiment under a pressure of 17.6 kPa (corresponding to a load of 180 gf/cm$^2$) and the thickness of the same diaper after unloading (no-load thickness) are such that the latter is 1.3 times or greater, particularly 1.5 to 3 times, the former (this ratio will hereinafter be referred to as a thickness ratio). Such a preferred thickness ratio is easily obtained by the use of the above-described foamed material. The thickness under load and the no-load thickness are measured according to the following methods.

The absorbent article is unfolded flat, and a test piece having a width of 100 mm parallel to the lateral direction and a length of 100 mm parallel the longitudinal direction of the article is cut out, the center of the test piece agreeing with the intersection of a line longitudinally dividing the article into two equal pieces and a line laterally dividing the article into two equal pieces. Where the longitudinal or lateral size of the absorbent article is smaller than 100 mm, the size of the absorbent article could be the size of the test piece. The test piece is placed on a horizontal mount and allowed to stand for 24 hours with no load applied. Then, an acrylic resin plate and a weight are put thereon, and the test piece is further allowed to stand under the load for 24 hours. The weight and size of the weight are decided so as to give the test piece a total load of 180 gf/cm$^2$ together with the acrylic resin plate. The acrylic resin plate used was 100 mm wide, 100 mm long, and 5 mm thick. After 24-hour load application, the thickness of each corner of the test piece under load is measured (measurement 1) to obtain an average thickness of the four corners, which is taken as a thickness under a load of 17.6 kPa.

The weight and the acrylic resin plate are removed, and the test piece is left to stand with no load applied. After 30 minute standing, an acrylic resin plate and a weight giving a total load of 98 Pa (corresponding to 1 g/cm$^2$) are placed thereon to flatten the test piece because any warpage or distortion of the test piece would hinder accurate thickness measurement. The weight and size of the weight used are decided so as to give the test piece a total pressure of 98 Pa together with the acrylic resin plate. The acrylic resin plate used was 100 mm wide, 100 mm long, and 5 mm thick. Immediately after putting the acrylic resin plate and the weight, the thickness of the test piece is measured in the same manner as in the measurement 1, and the average of the measured values of the four corners is taken as a no-load thickness.

In packaging the disposable diapers of the present embodiment, they are folded, stacked, compressed and packaged in a conventional manner. The thickness of the disposable diaper in the packaged state can be made equal to that of the one whose foamed material does not have the compressive recovery specified in the present invention but, upon being taken out of the package for use, the foamed material restores its thickness to satisfy the specified compressive recovery.

Constructed as described above, the disposable diaper of the present embodiment can be made thinner and more compact in a packaged state and, when taken out of the package for use, increases in thickness moderately. Therefore, the user can use the disposable diaper without feeling unreliability on account of lack of thickness. Even where urethane foam is used as the foamed material, the urethane foam used in the present embodiment hardly undergoes color change by ultraviolet rays or NO$_x$ gas and therefore gives no cause for deterioration of appearance.

Where a hot-melt adhesive is used in this embodiment as an adhesive for fixing the foamed material, the productivity in the manufacture of the disposable diapers increases, and there arises no problem of solvent remaining.

Another embodiment of the present invention provides a disposable diaper in which a leakproof sheet made of an ordinary material is used, the above-described foamed material is disposed between the leakproof sheet and the above-described absorbent member, and the sheet material used in the above-described first embodiment is disposed between the leakproof sheet and the foamed material. As demonstrated in Examples hereinafter given, this structure of the second embodiment is also effective in suppressing color change of the constituent member and making the color change, if any, invisible from the outside, thereby giving no cause for appearance deterioration. The sheet material used in this embodiment is not particularly limited in shape and size but, in order to prevent color change and to hide the color changed part, preferably has such a shape and a size that can completely cover the member (or the part) that is liable to color change. In this case, the sheet material is disposed and fixed at a prescribed position by, for example, adhesion with a hot-melt adhesive or heat sealing with the other member. Or, the sheet material can merely be disposed at a prescribed position without being fixed.

The absorbent article according to the present invention is by no means limited to the aforementioned embodiments. For example, while the present invention has been described with particular reference to a disposable diaper of the type which is folded into the shape of a diaper on use, the present invention is applicable to pants type disposable diapers, sanitary napkins, incontinence pads, and the like as well.

In the aforementioned embodiments, while the sheet material is used as a leakproof sheet or interposed between an ordinary leakproof sheet and the foamed material, in cases where there are a plurality of parts susceptible to color change, the sheet material can be used for each of such parts.

The above-described sheet material is useful not only as the constituent member of absorbent articles as has been described but as a material of hygienic articles, medical articles or clothing, such as disposable sheets or pillow covers for medical care.

EXAMPLES

The present invention will now be illustrated in greater detail with reference to Examples. The following Examples are presented as being exemplary of the present invention and should not be considered as limiting.

Examples 1 to 6

A hot-melt adhesive was compounded from the components shown in Table 1 below, whose melt viscosity is also shown in Table 1. The resulting hot-melt adhesive was applied substantially uniformly on a side (351 cm$^2$) of the foamed material shown in Table 2 below by spiral spraying at a hot air temperature of 150° C. under a spray pressure of 1.8 kg/cm² to make a spiral pattern having a spiral thickness of 0.3 mm. The coating weight was 5 g/m², and the area ratio of the coated part to the uncoated part was 4/6, i.e., the area of the coated part in 351 cm² was 140 cm². The adhesive-applied foamed material was adhered to supporting paper enclosing an absorbent member. A leakproof sheet having a moisture permeability of 1.5 g/(100 cm²·hr) measured according to JIS Z 0208 was fixed to the other side of the foamed material. A disposable diaper shown in FIGS. 1 through 4 was prepared in a conventional manner using conventional materials, except for using each of the resulting absorbent member/foamed material/leakproof sheet structures.

TABLE 1

Hot-Melt Adhesive

| Composition | | |
|---|---|---|
| Base polymer | SIS*¹ | 20 parts |
| Tackifier | Hydrogenated terpene resin*² | 65 parts |
| Softener | Process oil*³ | 15 parts |
| Antioxidant | Hindered phenol*⁴ | 0.3 part |
| Melt viscosity*⁵ (180° C.) (mPa · s) | | 2000 |

Note:
*¹Krayton D1117, available from Shell Chemical Company
*²Clearon P105, available from Yasuhara Chemical Co., Ltd.
*³PW-90, available from Idetmitsu Petrochemical Co., Ltd.
*⁴Irganox 1010, available from Chiba Geigy, Ltd.
*⁵Measured with a B type viscometer supplied by Tokyo Keiki K.K.

A disposable diaper was prepared in the same manner as in Example 1, except that the entire surface (351 cm²) on one side of the foamed material shown in Table 2 was coated solid (coated area/funcoated area ratio: 10/0) with the hot-melt adhesive at a spread of 10 g/m², and the foamed material was adhered to supporting paper having an absorbent member enveloped therein.

In Table 2 are shown the material, density, initial thickness (thickness before compression), and compressive recovery of the foamed materials used in Examples 1 to 6 and Comparative Example 1, and the thickness under load, no-load thickness, and thickness ratio (ratio of no-load thickness to the thickness under load) of the disposable diaper having the foamed material, and the results of evaluation on whether the diaper gave a wearer a humid feeling (bad) or not (good). The thickness under load and no-load thickness of the diaper were measured in accordance with the above-described methods.

TABLE 2

| | | Foamed Material | | | Diaper Thickness | | | |
|---|---|---|---|---|---|---|---|---|
| | Material | Density (kg/m³) | Initial Thickness (mm) | Compressive Recovery (%) | Under Load (mm) | No-load Thickness (mm) | Thickness Ratio | Humid Feeling |
| Example 1 | ether type urethane foam | 13.5 | 2.00 | 94 | 3.0 | 5.1 | 1.70 | good |
| Example 2 | ether type urethane foam | 15.7 | 2.00 | 95 | 3.0 | 5.1 | 1.70 | good |
| Example 3 | ether type urethane foam | 15.7 | 1.50 | 95 | 2.8 | 4.6 | 1.64 | good |
| Example 4 | ether type urethane foam | 15.7 | 1.00 | 96 | 2.5 | 4.2 | 1.68 | good |
| Example 5 | ether type urethane foam | 18.1 | 2.00 | 94 | 3.0 | 5.2 | 1.73 | good |
| Example 6 | ester type urethane foam | 26.0 | 2.30 | 99 | 3.0 | 5.3 | 1.77 | good |
| Comparative Example | ether type urethane foam | 13.5 | 2.00 | 94 | 3.0 | 4.8 | 1.60 | bad |

As is apparent from Table 2, the disposable diapers of Examples 1 to 6, in which the foamed material having the hot-melt adhesive dispersively and uniformly applied to make coated parts and uncoated parts is fixed at a prescribed position, can be made compact when packaged and restore the thickness on being taken out of the package on use to give a user a feeling of assurance and also maintain moisture permeability (breathability). On the other hand, the comparative disposable diaper, in which the hot-melt adhesive has been applied solid to the foamed material, while satisfactory in compressive recovery, lacks breathability, giving a user a humid feeling. The same results were obtained from disposable diapers prepared in the same manner as in Examples 1 to 6, except that the hot-melt adhesive was applied in a line pattern instead of the spiral pattern, the line pattern comprising 20 lines each having a thickness of 0.05 mm per centimeter of a straight line drawn at right angles with an arbitrarily chosen line of the applied adhesive.

Preparation Examples 1 to 7 and Comparative Preparation Examples 1 to 9

Preparation of Urethane Foam:

Prescribed amounts of the stabilizers shown in Tables 3 and 4 below except tertiary phosphorous ester compounds were added to 100 parts of a polyester polyol (hydroxyl value: 86; average molecular weight: 1300), and the mixture was heated to dissolve at 60 to 80° C. for 2 to 6 hours while stirring. To the mixture were added 5 parts of water, 0.8 part of triethylenediamine, and 1 part of a silicone foam stabilizer to prepare a polyol component. To 100 parts of tolylene diisocyanate (TDI) were added a prescribed amount of the tertiary phosphorous ester shown in Tables 3 and 4 to prepare an isocyanate component.

A hundred parts of the thus prepared polyol component and 10 parts of the isocyanate component were mixed up, thoroughly stirred, and let to foam spontaneously to obtain a white foamed block having a density of 26 kg/m³. A 2 mm thick sheet was sliced from the block and cut to prepare square specimens of 150 mm by 150 mm. The specimen was irradiated with ultraviolet rays for 24 hours in a carbon arc fadeometer FAL-SH-C, supplied by Suga Shikenki K.K., and the yellowness index (YI) was measured with a color difference meter SZ-Σ80, supplied by Nippon Densyoku Kogyo K.K., in accordance with JIS K 7103:1977 (Testing methods for yellowness and change of yellowness index of plastics). The results obtained are shown in Tables 3 and 4.

Further, the specimen was allowed to stand in 200 ppm carbon monoxide gas (NO) for 5 hours, and the YI was measured in the same manner as described above. The results are shown in Tables 3 and 4.

TABLE 3

| | Stabilizers Added to Urethane Foam | | YI | |
|---|---|---|---|---|
| | Kind | Amount | UV | NO |
| Preparation Example | | | | |
| 1 | 2-(2'-hydroxy-5'-methylphenyl)benzotriazole | 1.0 | 33 | 27 |
| | Phenyldiisodecyl phosphite | 1.0 | | |
| | 1,6-hexamethylenebis(N,N-dimethylsemicarbazide) | 1.0 | | |
| 2 | 2-(2'-hydroxy-5'-methylphenyl)benzotriazole | 1.0 | 35 | 29 |
| | Diphenylnonylphenyl phosphite | 1.0 | | |
| | 1,1,5,5-tetramethylcarbohydrazide | 1.0 | | |
| 3 | 2-(2'-hydroxy-5'-methylphenyl)benzotriazole | 0.5 | 29 | 25 |
| | 2-(2'-hydroxy-3',5'-di-t-butylphenyl)benzotriazole | 0.5 | | |
| | triisodecyl phosphite | 1.0 | | |
| | 1,6-hexamethylenebis(N,,N-dimethylsemicarbazide) | 1.0 | | |
| Comparative Preparation Example | | | | |
| 1 | none | — | 55 | 75 |
| 2 | 2-(2'-hydroxy-5'-methylphenyl)benzotriazole | 1.0 | 48 | 60 |
| 3 | diphenylnonylphenyl phosphite | 1.0 | 46 | 58 |
| 4 | 1,6-hexamethylenebis(N,N-dimethylsemicarbazide) | 1.0 | 49 | 65 |
| 5 | 2-(2'-hydroxy-5'-methylphenyl)benzotriazole | 1.0 | 44 | 55 |
| | 1,6-hexamethylenebis(N,N-dimethylsemicarbazide) | 1.0 | | |

TABLE 4

| | Stabilizers Added to Urethane Foam | | YI | |
|---|---|---|---|---|
| | Kind | Amount | UV | NO |
| Preparation Example | | | | |
| 4 | 2-(2'-hydroxy-3',5'-di-t-butylphenyl)benzotriazole | 1.0 | 36 | 30 |
| | phenyldiisodecyl phosphite | 1.0 | | |
| | phenyl N-morpholinocarbazinate*[1] | 1.0 | | |
| 5 | 2-(2'-hydroxy-3',5'-di-alkylphenyl)benzotriazole | 1.0 | 30 | 25 |
| | diphenylnonylphenyl phosphite | 1.0 | | |
| | phenyl 1,1-dimethylcarbazinate*[2] | 1.0 | | |
| 6 | 2-(2'-hydroxy-5'-methyl-phenyl)benzotriazole | 1.0 | 32 | 37 |
| | triisooctyl phosphite | 1.0 | | |
| | 1,6-hexamethylenebis(N-morpholinocarbamide)*[3] | 1.0 | | |
| 7 | 2-(2'-hydroxy-3',5'-di-t-butylphenyl)benzotriazole | 0.5 | 29 | 24 |
| | 2-(2'-hydroxy-3',5'-dialkylphenyl)benzotriazole | 0.5 | | |
| | phenyldiisodecyl phosphite | 1.0 | | |
| | 1,6-hexamethylenebis(N,N-cyclopentylenesemicarbazide)*[4] | 1.0 | | |
| Comparative Preparation Example | | | | |
| 6 | 2-(2'-hydroxy-5'-methylphenyl)benzotriazole | 1.0 | 48 | 62 |
| | adipic acid hydrazide | 1.0 | | |
| | tris(nonylphenyl)phosphite | 1.0 | | |
| 7 | adipic acid dimethylhydrazide | 3.0 | 55 | 60 |

TABLE 4-continued

|   | Stabilizers Added to Urethane Foam | | YI | |
|---|---|---|---|---|
|   | Kind | Amount | UV | NO |
| 8 | 2-(2'-hydroxy-5'-methylphenyl)benzotriazole | 1.0 | 43 | 55 |
|   | diphenylnonylphenyl phosphite | 1.0 | | |
| 9 | diphenylnonylphenyl phosphite | 1.0 | 50 | 57 |
|   | 1,1,5,5-tetramethylcarbohydrazide | 1.0 | | |

Note:

Example 7 and Comparative Example 2

The same hot-melt adhesive as used in Example 1 (see Table 1) was applied substantially uniformly on a side of a sheet of the urethane foam block prepared in Preparation Example 1 or Comparative Preparation Example 1 by spiral spraying at a hot air temperature of 150° C. under a spray pressure of 1.8 kg/cm² to make a spotted pattern having a coating weight of 5 g/m². The foam sheet was adhered to an absorbent member enveloped in supporting paper. A leakproof sheet having a moisture permeability of 1.5 g/(100 cm²·hr) as measured according to JIS Z 0208 was fixed to the other side of the foam sheet. A disposable diaper shown in FIGS. 1 through 4 was prepared in a conventional manner using conventional materials, except for using each of the resulting absorbent member/foamed materialaeakproof sheet structures.

In Table 5 are shown the kind, density, initial thickness (no-load thickness) and compressive recovery of the urethane foam used in Example 7 and Comparative Example 2 and the thickness under load, no-load thickness and thickness ratio of the disposable diaper having the urethane foam.

The resulting disposable diaper was irradiated with ultraviolet rays from its leakproof sheet side for 24 hours in a carbon arc fadeometer, and the change of appearance of the diaper due to the color change of the urethane foam as observed with the naked eye was rated according to the following A-to-C scale. The results obtained are also shown in Table 5.

A The urethane foam underwent no yellowing, giving no influence on the diaper appearance.

B The yellowing of the urethane foam was slightly perceived from the outside.

C The yellowing of the urethane foam was clearly perceived from the outside.

TABLE 5

|   |   | Urethane Foam | | | Thickness of Diaper (mm) | | | |
|---|---|---|---|---|---|---|---|---|
|   |   | | Initial | | | | | |
|   | Kind | Density (kg/m²) | Thickness (mm) | Compressive Recovery (%) | Under Load | No-load | Thickness Ratio | Appearance of Diaper |
| Example 7 | Preparation Example 1 | 26 | 2 | 99 | 3.0 | 5.3 | 1.77 | A |
| Comparative Example 2 | Comparative Preparation Example 1 | 26 | 2 | 99 | 3.0 | 5.3 | 1.77 | C |

It can be seen from the results in Table 5 that the disposable diaper of Example 7 having disposed in a prescribed position thereof a specific urethane foam that hardly yellows when exposed to $NO_x$ gas or ultraviolet rays can be made compact when packaged but increases its thickness when taken out of the package on use to give a user a feeling of assurance. It is also understood that the specific urethane foam hardly undergoes color change by ultraviolet rays, etc. Further, while not shown in Table 5, the disposable diaper of Example 7retained moisture permeability, not creating a humid internal environment.

Preparation Examples 8 to 13
Preparation of Moisture Permeable Sheet:
1) Preparation of Resin Composition The components shown in Table 6 below were compounded in a 100-liter Henschel mixer, kneaded in a twin-screw extruder (PCM-45-33.5, supplied by Ikegai Corp.; diameter: 45 mm) at a set temperature of 160° C. and at 150 rpm, and pelletized.

TABLE 6

| Prepn. Example No. | Polyolefin Resin | Filler | Plasticizer | Titanium Oxide | UV Absorber |
|---|---|---|---|---|---|
| 8 | 36 | 57 | 4 | 3 | 0 |
| 9 | 35 | 55 | 4 | 6 | 0 |
| 10 | 33 | 51.5 | 3.5 | 12 | 0 |
| 11 | 30.5 | 48 | 3.5 | 18 | 0 |
| 12 | 35.5 | 57 | 4 | 3 | 0.5 |
| 13 | 30.5 | 65 | 4 | 0 | 0.5 |

Note:
Polyolefin resin: Linear low-density polyethylene Ultzex 2520F, available from Mitsui Chemical; density: 0.925; MFR: 2.3 g/10 min
Filler: calcium carbonate Liton 22S, available from Bihokufunka Kogyo K.K.; average particle size: 1 μm
Plasticizer: polyester comprising trimethylolpropane, adipic acid and stearic acid = 3.5/2.5/5.5 by mole); saponification value: 265; acid value: 1.2; hydroxyl value: 8.6
Titanium oxide: particle size: 0.23 to 0.26 μm
UV absorber: 2-(2'-hydroxy-3'-t-butyl-5'-methylphenyl)-5-chlorobenzotriazole, Tinuvin-326, available from Chiba Specialty Chemicals 2) Film Formation The pellets were blow molded into a tubular film having a film thickness of 45 μm and a flat width of 390 mm by use of a blow molding machine comprising a single screw extruder (D: 50 mm; L/D: 28) and a circular die (D: 100 mm; lip clearance: 1 mm) under conditions of a set temperature of 160° C., a throughput of 25 kg/hr, and a blow-up ratio of 2.5 to obtain a film having a basis weight of 40 g/m².

3) Orientation

The blown film was uniaxially orientated 2.1 times to obtain a moisture-permeable sheet having a thickness of 20 μm and a basis weight of 20 g/m². The orientation was carried out on an orientation machine composed of a preheating roll (diameter: 600 mm; width:600 mm; set at 80° C.), an orientation roll (diameter: 100 mm; width: 600 mm; 50° C.), an annealing roll (diameter: 600 mm; width: 600 mm; 80° C.), and a chill roll (diameter: 600 mm; width: 600 mm).

The ultraviolet transmittance, whiteness, total light transmittance, moisture permeability and water pressure resistance of the resulting moisture permeable sheet were measure by the methods previously described. The results obtained are shown in Table 7

TABLE 7

| Prepn. Example | UV Transmittance (%) | Whiteness | Total Light Transmittance (%) | Moisture Permeability (g/100cm²·hr) | Water Pressure Resistance (kPa) |
|---|---|---|---|---|---|
| 8 | 1 | 70.2 | 31.8 | 1.9 | 20 or more |
| 9 | 0 | 73.8 | 28.6 | 1.4 | 20 or more |
| 10 | 0 | 78.5 | 22.8 | 1.5 | 20 or more |
| 11 | 0 | 82.7 | 18.6 | 1.7 | 20 or more |
| 12 | 0 | 70.4 | 31.5 | 1.9 | 20 or more |
| 13 | 8 | 67.4 | 32.5 | 2.4 | 20 or more |

Examples 8 to 18

Disposable diapers shown in FIGS. 1 to 4 were prepared by using each of the moisture sheets obtained in Preparation Examples 8 to 13 as a leakproof sheet, air-through nonwoven fabric having a basis weight of 30 g/m² which was made up of core/sheath conjugate fiber comprising polypropylene as a core and polyethylene as a sheath as a topsheet, heat-rolled nonwoven fabric having a basis weight of 20 g/m² which was made up of polypropylene fiber as outer nonwoven fabric layer, the same urethane foam as used in Example 1 (see Table 2), and other members known in the art (Examples 8 to 13).

Separately, disposable diapers were prepared in the same manner as described above, except that a leakproof sheet formed of an ordinary material was used and that the moisture permeable sheet prepared in Preparation Examples 8, 9 and 11 to 13 was disposed between the leakproof sheet and the foamed material (urethane foam) (Examples 14 to 18).

The disposable diapers thus prepared were evaluated for the degree of color change by NO gas and by ultraviolet rays (UV) as follows. The results obtained are shown in Table 8.

1) Degree of color change by NO gas

The diaper was allowed to stand in 200 ppm NO gas for 5 hours, and the color change was observed and rated as follows.

A . . . Color change is not observed, giving no uneasy feeling to a user.

B . . . Slight color change is observed but gives no uneasy feeling to a user.

C . . . Color change is perceived, giving a user a slight uneasy feeling.

D . . . Color change is clearly perceived, giving a user a great uneasy feeling.

2) Degree of Color Change by UV Rays

The diaper was irradiated with ultraviolet rays for 24 hours in a carbon arc fadeometer, and the color change was observed and rated as follows.

A . . . Color change is not observed, giving no uneasy feeling to a user.

B . . . Slight color change is observed but gives no uneasy feeling to a user.

C . . . Color change is perceived, giving a user a slight uneasy feeling.

D . . . Color change is clearly perceived, giving a user a great uneasy feeling.

TABLE 8

| Example No. | Moisture Permeable Sheet | Usage of Moisture Permeable Sheet | Color Change NO | Color Change UV |
|---|---|---|---|---|
| 8 | Prepn. Example 8 | used as a leakproof sheet | B | A |
| 9 | Prepn. Example 9 | used as a leakproof sheet | A | A |
| 10 | Prepn. Example 10 | used as a leakproof sheet | A | A |
| 11 | Prepn. Example 11 | used as a leakproof sheet | A | A |
| 12 | Prepn. Example 12 | used as a leakproof sheet | A | A |
| 13 | Prepn. Example 13 | used as a leakproof sheet | B | A |
| 14 | Prepn. Example 8 | disposed between the leakproof sheet and the foamed material | B | A |
| 15 | Prepn. Example 9 | disposed between the leakproof sheet and the foamed material | A | A |
| 16 | Prepn. Example 11 | disposed between the leakproof sheet and the foamed material | A | A |
| 17 | Prepn. Example 12 | disposed between the leakproof sheet and the foamed material | A | A |
| 18 | Prepn. Example 13 | disposed between the leakproof sheet and the foamed material | B | A |

As described above, the absorbent article according to the present invention is compact in a packaged state and increases its thickness on being taken out of the package to make a user feel assured. Further, the absorbent article of the present invention maintains moisture permeability. Even though urethane foam is used as a foamed material, the urethane foam used in the present invention hardly undergoes color change by ultraviolet rays or $NO_x$ gas. If any color change occurs, it does not impair the appearance of the absorbent article because it is hardly detected from the exterior. Furthermore, the absorbent article of the present invention is, being excellent in moisture permeability and water resistance, effective in preventing creation of a humid internal environment and resultant skin irritation.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid permeable topsheet, a liquid-impermeable and moisture-permeable leakproof sheet, and a liquid retentive absorbent member interposed between said topsheet and said leakproof sheet, wherein a foamed material is disposed between said leakproof sheet and said absorbent member, between said topsheet and said absorbent member, inside said absorbent member or in plural positions thereof, said foamed material having a density of 5 to 35 kg/m$^3$, a no-load thickness of 1 to 10 mm, and a compressive recovery of 60% or more in terms of (b/a×100), wherein a is a thickness (mm) measured after 24-hour standing with no load applied, and b is a thickness (mm) measured after 24-hour compression under a load of 180 gf/cm$^2$ followed by 30-minute standing with no load applied, and said foamed material is fixed at a prescribed position with an adhesive which has been applied to substantially the entire surface of at least one side of said foamed material or substantially the entire contact area of a member to be brought into contact with said foamed material in such a manner that the adhesive is distributed substantially uniformly while providing applied parts and unapplied parts, and wherein said foamed material is urethane foam.

2. An absorbent article according to claim 1, wherein the configuration of said applied parts is spots, lines, dots or spirals.

3. An absorbent article according to claim 1, wherein said adhesive is a hot-melt adhesive having a melt viscosity of 10,000 mPa·s or less at 180° C., and said hot-melt adhesive is applied to a coating weight of 1 to 30 g/m$^2$.

4. An absorbent article according to claim 1, wherein said urethane foam has an yellowness index of 40 or smaller when allowed to stand in 20 ppm nitrogen monoxide for 5 hours and when irradiated with ultraviolet rays in a carbon arc fadeometer for 24 hours.

5. An absorbent article according to claim 4, wherein said urethane foam contains, as stabilizers, (1) an ultraviolet absorber comprising a benzotriazole derivative, (2) a tertiary phosphorous ester represented by formula (I):

wherein $R_1$, $R_2$, and $R_3$, which may be the same or different, each represent an alkyl group, a cycloalkyl group, an aryl group, an alkylaryl group or an arylalkyl group, and having a phosphorus content of 4 to 14% by weight, and (3) a 1,1-dialkyl-substituted semicarbazide or carbazinic acid ester having a moiety represented by formula (II), (III) or (IV):

wherein $R_4$ and $R_5$, which may be the same or different, each represent a substituted or unsubstituted alkyl group having 1 to 10 carbon atoms, or $R_4$ and $R_5$ are taken together to form a ring which may contain a hetero atom.

6. An absorbent article according to claim 5, wherein said tertiary phosphorous ester has a phosphorus content of 6 to 8% by weight.

7. An absorbent article according to claim 1, wherein said leakproof sheet is made of a sheet material having an ultraviolet transmittance of 10% or less, a whiteness of 65 or more, and a total light transmittance of 35% or less.

8. An absorbent article according to claim 7, wherein said sheet material has a moisture permeability of 0.5 to 4 g/(100 cm$^2$·hr) and a water pressure resistance of 4.9 kPa or more.

9. An absorbent article according to claim 8, wherein said sheet material contains 1 to 25% by weight of titanium oxide.

10. An absorbent article according to claim 8, wherein said sheet material is an orientated polyolefin film obtained by molding a film from a resin composition comprising a polyolefin resin, titanium oxide, an ultraviolet absorber, and an inorganic filler and orientating the resulting film.

11. An absorbent article according to claim 7, wherein said foamed material is urethane foam, and said urethane foam is disposed between said absorbent member and said leakproof sheet.

12. An absorbent article according to claim 1, wherein said foamed material is urethane foam, said urethane foam is disposed between said absorbent member and said leakproof sheet, and a sheet material is disposed between said leakproof sheet and said foamed material, said sheet material having an ultraviolet transmittance of 10% or less, a whiteness of 65 or more, and a total light transmittance of 35% or less.

13. An absorbent article according to claim 7, wherein said sheet material contains 0.2 to 1.0% by weight of an ultraviolet absorber.

* * * * *